(12) United States Patent
Fouras et al.

(10) Patent No.: US 9,025,849 B2
(45) Date of Patent: *May 5, 2015

(54) PARTICAL IMAGE VELOCIMETRY SUITABLE FOR X-RAY PROJECTION IMAGING

(75) Inventors: Andreas Fouras, Park Orchards (AU); Stephen Dubsky, Carnegie (AU)

(73) Assignee: Monash University, Clayton (AU)

( * ) Notice: Subject to any disclaimer, the term of this patent is extended or adjusted under 35 U.S.C. 154(b) by 119 days.

This patent is subject to a terminal disclaimer.

(21) Appl. No.: 13/588,291

(22) Filed: Aug. 17, 2012

(65) Prior Publication Data

US 2013/0070062 A1  Mar. 21, 2013

Related U.S. Application Data

(63) Continuation-in-part of application No. 13/496,322, filed as application No. PCT/AU2010/001199 on Sep. 16, 2010.

(30) Foreign Application Priority Data

Sep. 16, 2009 (AU) ................................ 2009904481

(51) Int. Cl.
G06K 9/00 (2006.01)
H04N 13/02 (2006.01)
H04N 5/32 (2006.01)
(Continued)

(52) U.S. Cl.
CPC ........ *H04N 13/0203* (2013.01); *H04N 13/0242* (2013.01); *H04N 13/0253* (2013.01); *A61B 6/032* (2013.01); *A61B 6/481* (2013.01); *A61B 6/484* (2013.01); *A61B 6/486* (2013.01); *A61B 6/504* (2013.01); *A61B 6/5205* (2013.01);
(Continued)

(58) Field of Classification Search
None
See application file for complete search history.

(56) References Cited

U.S. PATENT DOCUMENTS

| 5,491,642 A | 2/1996 | Wormell et al. |
| 2005/0059876 A1* | 3/2005 | Krishnan et al. .............. 600/407 |
| 2010/0041992 A1 | 2/2010 | Ohuchi et al. |

FOREIGN PATENT DOCUMENTS

| DE | 199 48 827 A1 | 4/2001 |
| KR | 10-2004-0065846 A | 7/2004 |

OTHER PUBLICATIONS

A. Fouras, M.J. Kitchen, S. Dubsky, R.A. Lewis, S.B. Hooper, and K. Hourigan, "The past, present, and future of x-ray technology for in vivo imaging of function and form", May 19, 2009, Journal of Applied Physics 105, 102009, pp. 1-14.*

(Continued)

*Primary Examiner* — Aaron W Carter
*Assistant Examiner* — Siamak Harandi
(74) *Attorney, Agent, or Firm* — Sughrue Mion, PLLC

(57) ABSTRACT

A 2D or 3D velocity field is reconstructed from a cross-correlation analysis of image pairs of a sample, without first reconstructing images of the sample spatial structure. The method can be implemented via computer tomographic x-ray particle image velocimetry, using multiple projection angles, with phase contrast images forming dynamic speckle patterns. Estimated cross-correlations may be generated via convolution of a measured autocorrelation function with a velocity probability density function, and the velocity coefficients iteratively optimized to minimize the error between the estimated cross-correlations and the measured cross-correlations. The method may be applied to measure blood flow, and the motion of tissue and organs such as heart and lungs.

7 Claims, 10 Drawing Sheets

(51) Int. Cl.
    A61B 6/03       (2006.01)
    A61B 6/00       (2006.01)
(52) U.S. Cl.
    CPC .............. *A61B6/5235* (2013.01); *H04N 5/32* (2013.01); *A61B 6/507* (2013.01)

(56)             References Cited

OTHER PUBLICATIONS

S. Dubsky, et al., "Computed tomographic X-ray velocimetry for simultaneous measurement of 3D velocity and object geometry in opaque vessels", 15th Int Symp on Applications of Laser Techniques to Fluid Mechanics, Lisbon, Portugal, Jul. 5-8, 2010, pp. 1-12.
S. C. Irvine, et al., "Phase retrieval for improved three-dimensional velocimetry of dynamic x-ray blood speckle", Applied Physics Letters, 2008, pp. 153901-1-153901-3, vol. 93.
Stephen Dubsky, et al., "Three component, three dimensional X-ray particle image velocimetry using multiple projections", 14th Int Symp on Applications of Laser Techniques to Fluid Mechanics, Lisbon, Portugal, Jul. 7-10, 2008, pp. 1-11.
A. Fouras, et al., "In-vivo Synchrotron PIV for the measurements of airway motion",8th International Symposium on Particle Image Velocimetry -PIV09, Melbourne, Victoria, Australia, Aug. 25-28, 2009, 4 pages.
F. Zhang et al., "Evaluation of Segmentation Algorithms for Vessel Wall Detection in Echo Particle Image Velocimetry", International Ultrasonics Symposium Proceedings (IUS), 2009 IEEE International, Piscataway, NJ, USA, Sep. 20, 2009, pp. 2476-2479, XP031654536, ISBN: 978-1-4244-4389-5, Figure 1.
K. Wong et al., "Cardiac flow component analysis", Medical Engineering & Physics, Butterworth-Heinemann, GB, Mar. 1, 2010, vol. 32, No. 2, pp. 174-178, XP02694909, ISSN: 1350-4533, DOI: 10.1016/J. Medengphy, 2009.11.007. Figure 6(a).
A.J. Barker et al., "3-Component Phase-Contrast MRI WSS Vectors in the Carotid Bifurcation are Concurrent with Local Atherosclerotic Plaque Risk Hypotheses", 18th Annual Meeting of the International Society for Magnetic Resonance in Medicine, Stockholm, Sweden, vol. 5, May 1-7, 2010, XP040615221, 2 total pages, Figure (g).
J. Lu et al., "Blood flow velocity and ultra-filtration velocity measured by CT imaging system inside a densely bundled hollow fiber dialyzer", International Journal of Heat and Mass Transfer, Pergamon Press, GB, vol. 53, Nos. 9-10, Apr. 1, 2010 , pp. 1844-1850, XP026913421, ISSN: 0017-9310, DOI: 10.1016/J. IJHEATMASSTRANSFER.2010.01.005, Figure 11.
J. Choi et al., "Numerical Study of High-Frequency Oscillatory Air Flow and Convective Mixing in a CT-Based Human Airway Model", Annals of Biomedical Engineering, Kluwer Academic Publishers-Plenum Publishers, NE, vol. 38, No. 12, Jul. 8, 2010, pp. 3550-3571, XP019860722, ISSN: 1573-9686, DOI: 10.1007/S10439-010-0110-7, Figure 11.
A. Docef et al., "Deformed CT reconstruction from limited projection data", International Congress Series 1281, Cars & Elsevier B.V., 2005, pp. 104-108, DOI: 10.1016/j.ics.2005.03.263.
C. Soussen et al., "Polygonal and Polyhedral Contour Reconstruction in Computed Tomography", IEEE Transactions on Image Processing, vol. 13, No. 11, Nov. 2004, pp. 1507-1523.
Kim et al., "X-ray PIV measurements of blood flows without tracer particles", Experiments in Fluids, vol. 41, Apr. 27, 2006, pp. 195-200, DOI: 10.1007/s00348-006-0147-4.
Y. Yin et al., "Simulation of pulmonary air flow with a subject-specific boundary condition", J Biomech., NIH Public Access, vol. 43, No. 11, Aug. 10, 2010, 14 total pages, DOI: 10.1016/j.jbiomech. 2010.03.048.
A. Fouras et al., "Three-dimensional synchrotron x-ray particle image velocimetry", Journal of Applied Physics, vol. 102, 2007, 7 total pages, DOI: 10.1063/1.2783978.
T. Guerrero et al., "Dynamic ventilation imaging from four-dimensional computed tomography", Institute of Physics Publishing, Physics in Medicine and Biology, IOP Publishing Ltd., vol. 51, Jan. 25, 2006, pp. 777-791, DOI: 10.1088/0031-9155/51/4/002.
G. Christensen et al., "Tracking lung tissue motion and expansion/compression with inverse consistent image registration and spirometry", Medical Physics, vol. 34, No. 6, Jun. 2007, pp. 2155-2163.
B. Simon, "Regional Ventilation and Lung Mechanics Using X-Ray CT", CT Ventilation and Lung Mechanics, Academic Radiology, vol. 12, No. 11, Nov. 2005, pp. 1414-1422.
A. Fouras et al., "Engineering Imaging: Using Particle Image Velocimetry to See Physiology in a New Light", Clinical and Experimental Pharmacology and Physiology, Frontiers in Research, 2009, pp. 238-247.

* cited by examiner

Figure 11A
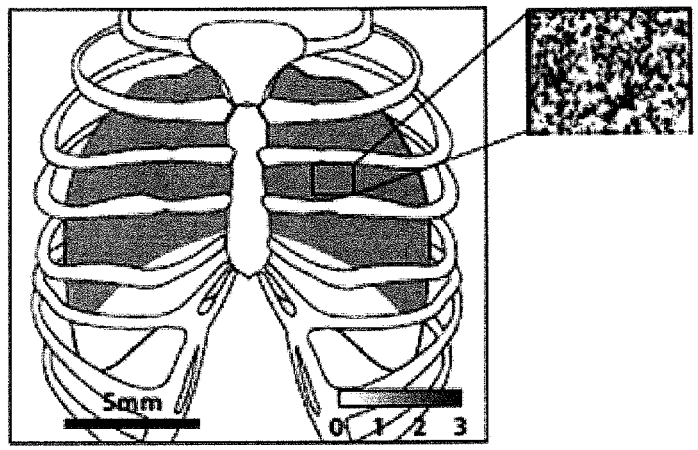
Figure 11C
Figure 11B
Figure 11D
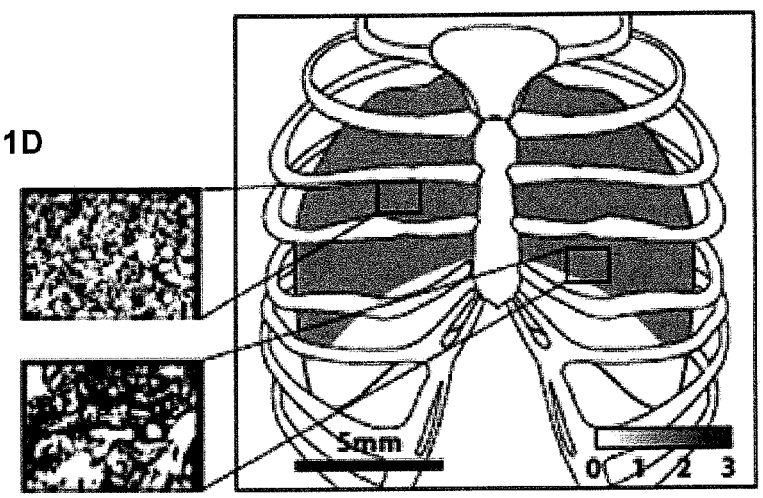
Figure 11E

PARTICAL IMAGE VELOCIMETRY SUITABLE FOR X-RAY PROJECTION IMAGING

FIELD OF INVENTION

The present invention relates to imaging, particularly imaging of movement.

In one aspect the present invention relates to the field of biomedical engineering, particularly in vivo or in vitro imaging.

In another aspect, the invention relates to technology for imaging of function and form in a wide range of research, medical and industrial applications.

In a yet further aspect the present invention is suitable for use as a method and device for imaging the movement of living tissue.

It will be convenient to hereinafter describe the invention in relation to in vivo medical imaging, however it should be appreciated that the present invention is not limited to that use only and can also be used for in vitro applications, and other medical applications such as diagnosis and treatment as well as research applications and industrial applications. In particular although the description will particularly refer to the pulmonary system and vascular system, the skilled person will appreciate that the application of the present invention is not so limited and can be extended to other systems that have a mechanically dynamic aspect to their function.

Furthermore, although it will be convenient to hereinafter describe the invention in relation to imaging using a source that emits X-rays, such as those used for computer tomographic X-ray particle image velocimetry (CTXV), it will be appreciated that the present invention extends to any system that provides imagery using any convenient source.

Many important processes in the human body involve motion. Obvious examples include the cardiovascular system (motion of heart and blood flow), the pulmonary system (motion of the diaphragm and lungs), the renal system (motion and filtering of blood) and the musculoskeletal system (motion of muscles, connective tissue, bones and joints). Diseases of the vascular system such as thrombus formation and pulmonary disease are leading causes of mortality and morbidity in developed countries. Studying the mechanically dynamic aspects of these systems contributes to better understanding of the fundamental operation of the human body and is a useful aid to the combat of dysfunction and disease.

The ability to recognise and treat disease or dysfunction in these systems is dictated by our ability to image them in situ with high resolution. In particular, current imaging cannot reveal most forms of lung disease before they become clinically evident. The earlier these diseases are detected, the better the prognosis.

A relatively common feature of many lung diseases such as emphysema and pulmonary fibrosis is a regional alteration to the distal airway structure leading to marked regional changes in lung tissue compliance. Thus attempts have been made to develop imaging techniques that can detect regional differences in tissue velocities across the lung during the respiratory cycle and thus detect lung disease and dysfunction in their early stages.

BACKGROUND ART

It is to be appreciated that any discussion of documents, devices, acts or knowledge in this specification is included to explain the context of the present invention. Further, the discussion throughout this specification comes about due to the realisation of the inventor and/or the identification of certain related art problems by the inventor. Moreover, any discussion of material such as documents, devices, acts or knowledge in this specification is included to explain the context of the invention in terms of the inventor's knowledge and experience and, accordingly, any such discussion should not be taken as an admission that any of the material forms part of the prior art base or the common general knowledge in the relevant art in Australia, or elsewhere, on or before the priority date of the disclosure and claims herein.

It will also be appreciated that references herein to 'motion' are interchangeable with 'flow' or 'velocity' (being a function of motion over time).

The ability to measure three-dimensional (3D) blood flow fields in vivo is an important capability for studying the effects of blood flow properties on the development, diagnosis and treatment of cardiovascular diseases, such as atherosclerosis. To gain useful information from in vivo blood flow field measurements, non-invasive measurement through optically opaque tissue at high resolution is required.

The development of technologies underpinning in vivo measurements of form and function of the human body are discussed in various reviews. (See for example Fouras A, Kitchen M J, Dubsky S, Lewis R A, Hooper S B and Hourigan K 2009 *Journal of Applied Physics* Vol. 105).

Currently available techniques for flow field measurement in opaque vessels, such as magnetic resonance imaging based techniques, suffer from poor spatial and temporal resolution, limiting the application of these techniques for in vivo flow analysis. Better results have been achieved with techniques such as Particle image velocimetry (PIV) in which the displacement of tracer particles is determined using statistical cross-correlation of regions within particle image pairs. Several variants exist for volumetric flow analysis, including Tomographic PIV, volumetric particle tracking and Holographic PIV.

PIV Imaging Generally

PIV is well known for accurate measurement of instantaneous velocity fields. PIV techniques using visible light are limited to optically transparent sample. However the use of X-rays with PIV has extended the application of this method to opaque tissue, making this imaging mode ideal for in vivo blood flow field measurement.

In PIV, regions of fluid containing multiple tracer particles (typically illuminated by a visible wavelength laser) are imaged at two points in time, separated by a known time interval, and processed using correlation software. Specifically the image pairs are allocated into discrete interrogation regions. Cross correlation is performed between image pairs on each interrogation region and statistically, the maximum value of the cross correlation is the most likely particle displacement within the interrogation region.

In recent years PIV has been combined with X-ray imaging. The penetrating power of X-rays allows flow to be measured within opaque objects, with applications for non-invasive, high resolution blood flow field measurements.

2D Particle Image Velocimetry

Kim and Lee (Kim G B and Lee S J 2006, *Exp. Fluids* 41, 195) have measured flow in tubes with particles and blood cells as tracers using X-ray PIV. The methods taught in that study are limited to two components of the velocity (averaged over the dimension perpendicular to the image plane) within the measurement volume. The PIV algorithms used belonged to the prior art relating to optical/laser based velocimetry. These algorithms assume pulsed (instantaneous) illumination and zero out-of-plane flow gradients and therefore fail to take into account the 3D characteristics of imaging real flows using X-rays. This results in a significant under estimation of flow velocity.

3D Particle Image Velocimetry

Recently X-ray PIV analysis has been extended to include 3D flow data. Fouras et al (Fouras A, Dusting J, Lewis R and Hourigan K et al, 2009 Journal of Applied Physics Vol. 102: 064916) teach that the correlation peak represents a probability density function (PDF) of the velocity within the measurement volume. When combined with certain assumptions about the flow field, it is possible to convert this volumetric PDF of the velocity to a velocity profile. This results in the capability to measure 3D flow data from single projection X-ray images.

CT is a technique used to reconstruct an object in three-dimensional space from two dimensional projections. Typically, integrated object density in the projection direction is calculated from the X-ray attenuation, which will be proportional to the pixel intensity values on a digital projection image. The object structure is then reconstructed from projection images taken at different viewing angles, using Fourier back-projection or algebraic methods. Variants also exist for reconstruction of objects from few projection angles, which use iterative methods to reconstruct the sample's structure, often exploiting prior knowledge of the sample, for example that it is made up of a single material.

CTXV can thus deliver three component velocity measurements for complex 3D flow fields such as those found in the cardiovascular system. Single projection images are insufficient for evaluating three components of velocity. Images taken at a single projection angle contain no displacement information in the direction parallel to the X-ray beam. This limits single projection X-ray PIV to two component velocity measurements. In a method similar to CT, CTXV overcomes this limitation by using multiple projection angles. Signal-to-noise ratios can be enhanced using phase contrast imaging and phase retrieval methods.

Specifically, as in single projection X-ray PIV of the prior art, cross-correlation functions are calculated for interrogation regions within image pairs. The velocity field is reconstructed in axial slices, defined by the rows of interrogation regions for all projection angles. A three component, 2D, rectangular grid model represents the velocity field for each slice. Estimated cross correlation functions are generated for every angle and every interrogation region within each slice. The estimated cross-correlation functions are generated using convolution of the measured autocorrelation function with the velocity PDF for the interrogation region within the model. The velocity coefficients in the model are iteratively optimized, minimizing the error between measured cross-correlation function and the estimated cross-correlation functions, across all projection angles and interrogation regions simultaneously within that slice. Using this iterative approach, a model is reached which accurately represents the three component velocity field within each slice.

A relatively small number of projections are required and this is important for minimising radiation dosage. It also allows the integration of CTXV with a CT reconstruction such as described above, delivering simultaneous measurement of both form and function.

CT has the advantage of offering the best resolution and penetration of all medical imaging modalities, but also has the significant disadvantage of delivering high doses of X-rays. If not for this radiation dose concern high resolution CT would become a standard screening tool.

But even though they offer the best resolution and penetration of all medical imaging modalities, the X-ray PIV techniques of the prior art use particle images taken at a single viewing angle, which contain no particle displacement information in the direction parallel to the X-ray beam, and therefore they suffer the drawback that they are limited to two component velocity measurements. Also, no information regarding the velocity profile in the dimension perpendicular to the image plane is available, and therefore 3D measurements are not possible without prior knowledge of the flow.

There is an ongoing need to expand capabilities for measuring both form and function in terms of structure, volume and motion and provide a truer 3D reconstruction of flow fields.

SUMMARY OF INVENTION

An object of the present invention is to provide improved images that are truer 3D reconstructions rather than 3D image reconstructions.

A further object of the present invention is to provide an improved method of converting data sets into truer 3D reconstructions rather than 3D image reconstructions.

It is an object of the embodiments described herein to overcome or alleviate at least one drawback of related art systems or to at least provide a useful alternative to related art systems.

In essence, embodiments of the present invention stem from the realisation that imaging can utilise three components (u,v,w) of motion over 2, or preferably 3 spatial coordinates (x,y,z) plus time (t), which will be referred to herein as '3D' or '4D' as appropriate, but in practice measures more components than 3D imaging of the prior art. Furthermore, it has been realised that this methodology can be applied to measurement of motion of any kind. For example with reference to physiological measurements the methodology can be applied to measuring motion fluid, such as blood, air or lymph, and/or measurement of tissue, such as lung tissue during inspiration and expiration. A further realisation is that data relating to characteristics such as compliance and shear can also be processed. In practice, the present invention provides the ability to, (i) make 3D reconstructions of motion that are not possible using 3D imaging technology of the prior art, (ii) reconstruct 3D motion (velocity) information without first reconstructing 3D images, (iii) evaluate data such as shear, compliance and volume flow, in 4D (x,y,z,t) and present them in image format by reconstructing 3 components of velocity over 3D or 4D.

The present invention permits the extraction and manipulation of data to allow presentation of functional information in a format that is easy to compare and interpret. In particular it can be used for presentation of regional functional information. The term 'region' or 'regional' is used in the sense of functional information pertaining to an area or locale (such as, for example, a part of an organ such as a lobe of a lung), and may be used in contradistinction to functional information derived from a combination or average of data from multiple regions (such as, for example an entire organ, such as a lung). For example a region can be global, lobar, functional gas or fluid exchange units or any other desired segment or locale. Thus the present invention may be used to present functional information that is commonly used in scientific and clinical practice (such as FEV1) but has not hitherto been available regionally.

In a first aspect of embodiments described herein there is provided a method for imaging of a sample, the method including the steps of:

1. recording images from at least one projection angle and carrying out image pair cross-correlation analysis encoding velocity data for the sample in terms of coordinates; and
2. reconstructing a 2D or 3D velocity field directly from the image pair cross-correlations from the analysis wherein the reconstruction is performed without first reconstructing 2D or 3D images and wherein steps 1 and 2 are automated.

It should be noted that although the present invention will be described and exemplified with reference to Cartesian coordinates, it will be readily apparent to the person skilled in the art that other coordinate systems could be used and data could be converted from one coordinate system to another. For example, cylindrical or polar coordinates could be used, or local coordinates that are oriented to the relevant anatomy.

The reconstruction of step 2 may be carried out by iterative methods, or alternatively direct methods.

The image of the velocity field can thus convey a large amount of information visually. However velocity field images, while familiar to physicists, are not familiar to other professionals who may need to interpret them such as medical practitioners or pathologists who are used to seeing physiological features. In order to provide an image that is more readily recognised and understood, it may be necessary to associate the velocity field with corresponding features of a digitised (segmented) image of the sample. The need to associate image data with recognisable physiological or other features is not limited to velocity fields but can apply to any appropriate image data captured by any means.

There is further provided a method for providing an image of a sample comprising the steps of:
1. recording images encoding data for the sample in terms of coordinates;
2. reconstructing a 2D or 3D data field from the information encoded in the recorded images;
3(a) segmenting an image of the sample, and
3(b) associating each segment with regions of the 2D or 3D data field, wherein the reconstruction is performed without first reconstructing 2D or 3D images and wherein steps 1 and 2 are automated.

Preferably the images will be recorded from multiple angles. However, it will be apparent to the person skilled in the art (as disclosed in Irvine S C, Paganin D M, Dubsky S, Lewis R A and Fouras A 2008 *Applied Physics Letters* 93:153901; and Fouras, A., Lo Jacono, D., Nguyen, C. V. & Hourigan, K. 2009 Volumetric correlation PIV: a new technique for 3D velocity vector field measurement. *Experiments in Fluids* 47 (4), 569-577) that when a sample has rotational symmetry in terms of shape or motion, measurement from only one projection angle will be necessary. Furthermore, only one projection angle will be needed if depth data from phase or focus is recorded in addition to velocity data.

Accordingly, in a second aspect of embodiments described herein there is provided a method for imaging of a sample, the method including the steps of
1. recording images from at least one projection angle and carrying out image pair cross-correlation analysis to obtain 2D velocity data for the sample in terms of three coordinates, and
2. reconstructing a 3D velocity field directly from the image pair cross-correlations from the analysis wherein steps 1 and 2 are automated.

Using this method a 2D or 'single projection' image of the sample is thus obtained. By repeating the steps many times, the 3D data can be expanded to 4D data.

Accordingly, in a third aspect of embodiments described herein there is provided a method for imaging of a sample, the method including the steps of:
1. recording images from at least one projection angle and carrying out image pair cross-correlation analysis encoding velocity data for the sample in terms of coordinates; and
2(a) using an iterative method for reconstructing a 3D velocity field directly from the image pair cross-correlations from the analysis;
2(b) repeating the iterative method to produce a 4D velocity field; and
3. using the 4D velocity field to provide further information wherein the reconstruction is performed without first reconstructing 2D or 3D images and wherein steps 1 to 3 are automated.

The further information provided according to the above method may relate to any useful characteristic such as shear or compliance. These may be important to analysis of the degree or quality of functionality of the sample. In addition to recordal of velocity data, step 1 may include recordal of depth information from phase (holography) or focus.

Typically the iterative method will be analogous to an iterative CT method.

Any source that provides imagery can be used with the method of this invention. This includes sources that emit the following types of energy;

X-rays,
visible light including visible lasers,
infrared radiation including infrared lasers,
ultraviolet radiation including ultraviolet lasers,
ultrasound,
electrical impedance, and
magnetic resonance.

In a preferred embodiment the present invention is a method for CTXV imaging of a sample.

In a fourth aspect of embodiments described herein there is provided a method for imaging of a sample, the method including the steps of:
1(a) recording images from multiple projection angles;
1(b) allocating images into rectangular interrogation windows;
1(c) deriving velocity components u, v and w in the x, y and z directions from the images;
1(d) carrying out cross-correlation analysis on image pairs defined by the interrogation windows; and
2. reconstructing a 3D velocity field directly from the image pair cross-correlations derived from the analysis wherein the reconstruction is performed without first reconstructing 2D or 3D images and wherein steps 1 and 2 are automated.

In a fifth aspect of embodiments described herein there is provided a method for converting data sets defining a velocity field to a regional compliance map the method comprising the steps of:
1(a) recording images from at least one projection angle and carrying out image pair cross-correlation analysis to measure encoded parameters of,
(i) velocity (u, v and w) against time opposite Cartesian coordinates (x, y and z),
(ii) a further physical parameter (p) chosen from the group comprising pressure or volume;
2(a) integrating the measurements to provide a single 3D velocity field; and
2(b) describing regional compliance in terms of derivatives defined by $(\delta u/\delta x + \delta v/\delta y + \delta w/\delta z)/\delta p$ wherein step 2 is performed without first reconstructing 2D or 3D images and wherein steps 1 and 2 are automated.

In yet a further aspect of embodiments described herein there is provided a method for converting data sets defining a velocity field to a regional compliance map the method comprising the steps of:

1. recording images from at least one projection angle and carrying out image pair cross-correlation analysis to measure encoded parameters of,
   (i) motion (u and v) opposite Cartesian co-ordinates (x and y), and
   (ii) sample thickness (t), pressure (p) and volume (V);
2(a) integrating the measurements to provide a single 3D velocity field;
2(b) describing regional compliance in terms of $(\delta u/\delta x + \delta v/\delta y) \cdot t/\delta p$; and
2(c) solving for t, by mathematical comparison of total compliance with the total compliance determined by adding the regional compliances, according to, $$t = V/\Sigma/(\delta u/\delta x + \delta v/\delta y),$$

wherein step 2 is performed without first reconstructing 2D or 3D images and wherein steps 1 and 2 are automated.

For example, the above method could be used to create a regional compliance map for inspiration or expiration of a lung, beating of a heart, or pulsation of blood in an artery. Thus the present invention can be used for measuring any motion whether fluid or tissue.

With particular reference to the lung, the method of the present invention can be used to detect lung tissue movement and to measure the velocity fields that define speed and direction of regional lung motion throughout a breath. Regional maps of the lung can be generated showing degree and timing of expansion from the velocity fields, revealing regions of abnormal tissue properties caused by experimentally induced non-uniform lung disease. This includes diseases such as pulmonary fibrosis, cystic fibrosis, cancer and asthma.

Specifically, this would include measuring parameters of air velocity (u, v and w) against time opposite Cartesian coordinates (x, y and z), segmenting a 3D image of the airways of the lung, then associating each region of the lung over which velocity was measured with a corresponding segment of the 3D image to depict airflow within the airways over time. The flow chart at FIG. 12 summarises the aforementioned steps.

While the image of the velocity field can thus convey a large amount of information visually, as mentioned above, velocity field images are familiar to physicists, but are not familiar to other professionals who may need to interpret them. For example medical practitioners or pathologists are used to seeing physiological features or textual presentation (such as graphs or tables). In order to provide a textual or graphical presentation of functional information that is more readily recognised and understood, it may be necessary to associate the velocity field with indicia denoting different regions in the sample.

Accordingly, in a third aspect of embodiments described herein there is provided a method for presenting information derived from a sample, the method including the steps of:

1. recording images from at least one projection angle and carrying out image pair cross-correlation analysis encoding velocity data for the sample in terms of Cartesian coordinates;
2. reconstructing a 2D or 3D velocity field directly from the image pair cross-correlations from the analysis wherein the reconstruction is performed with or without first reconstructing 2D or 3D images; and
3. calculating the expansion of one or more regions in terms of velocity (u, v and w) against time opposite Cartesian co-ordinates (x, y and z) and using derivatives defined by $\delta u/\delta x + \delta v/\delta y + \delta w/\delta z$ for textual or graphical presentation.

Typically the method also includes the steps of segmenting an image of the sample and associating each segment with regions of the 2D or 3D data field. For example, segmentation can comprise obtaining relevant basic anatomical detail, such as details of the airways of the lung. The subject can then be subjected to a physiological manoeuvre such as forced expiration so that the regional airflow can be associated with the anatomical details. Hence steps 2 and 3 (mentioned above) can be used to calculate airflow throughout the airways of the lung. The calculations can be textually represented (or represented in an image) to display the volume of air expired in a short period of time (eg 1 second) in a single region, or multiple regions, or every region of the airway tree, thus providing a regional FEV1.

These function-based regional measurements or groups of regional measurements can be compared to one another.

Required anatomical detail of the lung can be obtained by any convenient method including:
high or low resolution CT scan of the subject's lung;
MRI scan, for example, spin density MRI;
direct application of anatomical atlas, optionally in conjunction with subject data such as height, weight, tidal volume;
matching data from an anatomical atlas to a plane radiograph or any other spectroscopic analysis of the subject's lungs;
combinations of the above methods.

Due to the functional capacity of the method of the present invention, previously unavailable in X-ray imaging, combined with the expectations of dramatic reduction in dose, an apparatus or system based on the method could find great utility, for example as a clinical scanner. Such a scanning system could be used to provide early detection and diagnosis of diseases or disorders. The apparatus could also be applied to industry, for example measuring motion in minerals processing, or in the laboratory for pre-clinical medicine, minerals processing, geophysics and fluid mechanics.

In another aspect of embodiments of the invention there is provided an apparatus when used for the method of the present invention, the apparatus comprising:
(i) one or more energy source;
(ii) one or more detectors for recording images created by energy from the one or more energy sources passing through a sample; and
(iii) a sample retainer for locating the sample intermediate the one or more energy sources and the one or more detectors;
wherein in use, the sample retainer rotates the sample through multiple energy projection angles and at least one image is recorded at each of the projection angles.

In another aspect of embodiments of the invention there is provided an apparatus when used for the method of the present invention, the apparatus comprising:
(i) one or more energy source; and
(ii) one or more detectors for recording images created by energy from the one or more energy sources passing through a sample;
wherein in use, a sample is located intermediate the one or more energy sources and the one or more detectors, the sources and detectors being rotated relative to the sample through multiple energy projection angles and at least one image of the sample is recorded at each of the projection angles.

In another aspect of embodiments of the invention there is provided an apparatus when used for the method of the present invention, the apparatus comprising:
(i) two or more energy sources having respective projection angles;
(ii) one or more detectors for recording images created by energy from the energy sources as it passes through a sample; and wherein recordings at each of the projection angles are made simultaneously.

Any convenient range of projection angles may be used from 1° to 360°. However, typically the range of projection angles does not reach the extremes of this range. For example, projection angles spaced over as little as 30° or as much as 180° are likely to be suitable.

In addition to at least one energy source and detector, the apparatus for use with the method of the present invention may include a number of other components including, for example, (i) systems for modulating and aligning the source, the target and/or the detector, (ii) systems for image capture, processing and analysis, and (iii) a convenient user interface.

Other aspects and preferred forms are disclosed in the specification and/or defined in the appended claims, forming a part of the description of the invention.

Although there are a number of prior art systems that can measure 3D velocity information such as Doppler ultrasound, magnetic resonance imaging (MRI), holographic PIV, digital in-line holographic PTV, tomographic PIV and defocusing PIV, these all have drawbacks not included in the present invention. For example, Doppler ultrasound has limited spatial and temporal resolution, the resolution decreasing with increased depth of measurement. MRI has limited spatial and temporal resolution, which is particularly evident in temporal measurement. Holographic PIV, digital in-line holographic PTV and tomographic PIV are limited to transparent media which virtually eliminates their utility for in-vivo imaging. The also cannot provide shape/anatomical information. Furthermore these techniques are based on reconstructing 4D images to then measure motion, which means that systems using these techniques are comparatively complex and have limited spatial resolution compared to the system of the present invention.

Compared with the aforementioned systems and other systems of the prior art, the present invention provides advantages that include the following:
the ability to decode far more information (the entire projected velocity probability density function) from an image pair than traditional CT can extract from an image (the line integrals of the X-ray absorption);
improved imaging with higher resolution as compared with prior art methods;
significant advancement in PIV technology, particularly X-ray PIV and holographic velocimetry;
improved ability to measure 3D motion fields in opaque samples, such as the lungs, heart and blood vessels;
comparatively short scan time, minimising sample exposure to the radiation source; and
new options for clinical diagnosis and treatment The present invention is suitable for a wide range of medical, biological and industrial applications. Within the medical and biological fields the present invention is particularly well suited to the study or measurement of motion associated with;
blood,
the heart and its valves,
lung tissue,
cilia including mucociliary clearance,
flow of air within the lungs and other tissue,
the gastrointestinal tract and its contents,
structures within the ear including the ear drum, cilia and bones,
fluid within the ear,
swelling, including brain swelling,
bones including synovial fluid and connective tissue at joints,
muscle, and
the lymphatic system including lymphatic fluid.

For example, the present invention could be used on lung tissue types to obtain regional functional information, including:
during forced expiratory manoeuvers;
peak inspiratory flow;
peak expiratory flow;
regional tidal volume;
expiratory reserve volume;
volume flow gradient
volume flow loops;
functional vital capacity.

The present invention can also be used to measure other functional parameters such as:
regional ventilation heterogeneity;
functional distribution;
gravitation distortion;
gravitation loading;
regional time constants of any measure, such as expiratory flow;
regional phase of any measure, such as expiratory flow;
time of peak of a measure;
time of minima of a measure;
determination of organ properties, such as lung properties (for example, strength of lung recoil or diaphragm action)

Additionally, the present invention could be used on a range of tissue types including the lung, but also including the heart, vasculature, lymph channels, brain.

All the above can be viewed globally or regionally and comparisons made between regions, groups of regions and the global measure.

Further scope of applicability of embodiments of the present invention will become apparent from the detailed description given hereinafter. However, it should be understood that the detailed description and specific examples, while indicating preferred embodiments of the invention, are given by way of illustration only, since various changes and modifications within the spirit and scope of the disclosure herein will become apparent to those skilled in the art from this detailed description.

BRIEF DESCRIPTION OF THE DRAWINGS

Further disclosure, objects, advantages and aspects of preferred and other embodiments of the present application may be better understood by those skilled in the relevant art by reference to the following description of embodiments taken in conjunction with the accompanying drawings, which are given by way of illustration only, and thus are not limitative of the disclosure herein, and in which:

FIG. 11A shows a regional expansion map determined using PIV for the lung of a typical control mouse.

FIG. 11B shows a regional expansion map determined using PIV for the lung of a mouse treated with bleomycin.

FIG. 11C shows a comparative histological image from the control mouse lung imaged in FIG. 11A.

FIG. 11D shows a comparative histological image from the left lung treated with bleomycin and imaged in FIG. 11B.

FIG. 11E shows a comparative histological image from the right lung treated with bleomycin and imaged in FIG. 11B;

DETAILED DESCRIPTION

Figure 1:
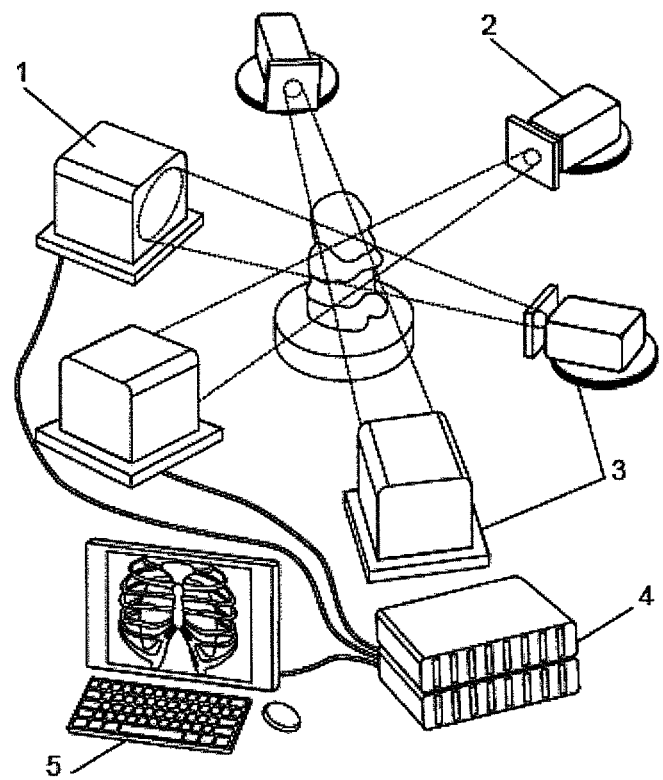
FIG. 1 is a schematic diagram outlining the basic design of a CTXV system according to the present invention. The diagram shows three polychromatic X-ray beams transmitted through a sample and converted to visible light by scintillators. High-speed detector systems then produce a set of images. Multiple projection data are gathered simultaneously without rotating the sample. Cartesian co-ordinates (x,y,z) are fixed to the sample and rotated at an angle θ from the beam axis p.

As mentioned above, Fouras et al. have demonstrated that the cross-correlation functions calculated from X-ray image pairs represent a velocity PDF for the projected measurement volume.

The present invention now provides a technique that includes imaging the flow from multiple projection angles to obtain information regarding the three components of velocity in three dimensional space. Using this information, the 3D velocity field can be reconstructed directly from image pair cross-correlations, without the need to reconstruct a volumetric image.

Further Uses of Data Collected

As discussed above the present invention is not limited to imaging the motion of fluid such as blood, but can also depict the motion of tissues or entire organs such as the lungs. Further quantitative processing of the data used for imaging can provide additional useful information such as the airflow within the lungs or the amount of shear.

The data collected can also be used to construct images of the shape/anatomy of a structure such as an organ simultaneously with velocity.

The present invention can also provide useful information relating to the periodic nature of a system such as breathing, heart beating or peristalsis. Specifically data collected at different points in time can be combined to reconstruct one cycle of, for example, a breath, a heart beat or peristaltic contraction.

The data collected according to the present invention may include depth information from phase (holographic) data or focus data. These types of data can be used to improve the quality of data representation for the same number of projections, or alternatively, reduced the number of projections from which data is gathered. At one limiting extreme, data could be collected from as few as one or two projections, however some data would be lost if a single projection was used. Accordingly, it is preferred that the method includes the steps of;
1. recording images from at least one projection angle, preferably multiple projection angles and carrying out image pair cross-correlation analysis encoding velocity data for the sample in terms of coordinates, and
2. reconstructing a 2D or 3D velocity field directly from the image pair cross-correlations from the analysis wherein the reconstruction is performed without first reconstructing 2D or 3D images and wherein steps 1 and 2 are automated.

Conversion of Data Sets into Compliance Maps

The present invention provides a method of converting data sets into regional compliance maps. For example, for lung ventilation the data set (defining a velocity field) may comprise measurement of velocity in either 2D or 3D, the lung pressure range over the course of a breath and possibly the volume of air inhaled and exhaled over the course of the patient taking a breath.

When the data set defines a 3D+time (ie 4D) velocity field the conversion method comprises the steps of;
1. recording images from at least one projection angle, preferably multiple projection angles and carrying out image pair cross-correlation analysis encoding velocity data for the sample in terms of Cartesian coordinates, and
2(a) integrating the velocity over any part of either the inspiration or expiration, to give a single 3D velocity field—this 3D map having quantities of velocity that can be defined as u, v and w over the directional co-ordinates x, y and z;
2(b) the regional compliance is then described mathematically as $$(\delta u/\delta x + \delta v/\delta y + \delta w/\delta z)/\delta p$$

(where $\delta p$=change in pressure over the same part of inspiration or expiration in 2a)

wherein the reconstruction of step 2 is performed without first reconstructing 2D or 3D images and wherein steps 1 and 2 are automated.

When the data set defines a 2D+time (ie 3D) velocity field the conversion method comprises the steps of;
2(a) integrating the velocity over all of either inspiration or expiration, to give a single 2D velocity field, this 2D map having quantities of velocity that can be defined as u and v over the directional co-ordinates x and y.
2(b) describing the regional compliance mathematically as:

$$(\delta u/\delta x + \delta v/\delta y) \cdot t/\delta p$$

(where t=thickness, p=pressure over inspiration or expiration)

2(c) solving for t, by mathematical comparison of total compliance (commonly measured) with the total compliance determined by adding the regional compliances, which in equation form can be expressed as;

$$t = V/\Sigma(\delta u/\delta x + \delta v/\delta y)$$

(where V=volume inhaled or exhaled)

wherein the reconstruction of this step 2 is performed without first reconstructing 2D or 3D images and is automated.

Figure 5:
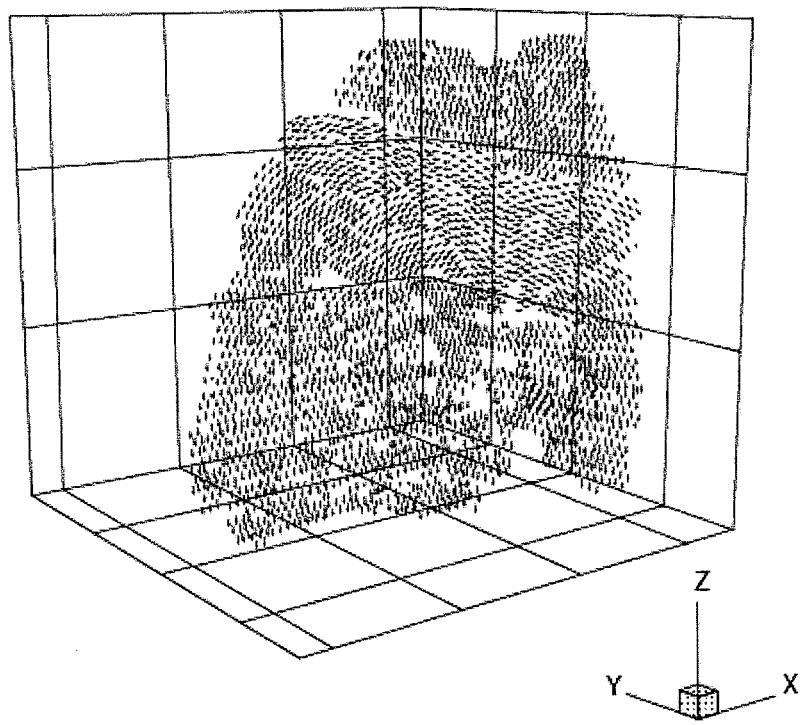
FIG. 5 is a velocity field of the type depicted in FIG. 4, for a lung and comprises vectors that show the velocity of lung tissue at a single time point during inspiration.

Using this method a vector field image of the type in FIG. 5 can be produced. In this image, vectors show the velocity of lung tissue at a single time point during inspiration, measured using CTXV. Different shades of grey (or preferably, different colours) can be used to represent velocity magnitude and the vector resolution reduced in all dimensions aids visualisation. In this image the spacing between velocity measurements is approximately 0.18 mm. This illustrates that CTXV is capable of producing high-resolution, accurate measurements with very few projections.

By relating the vector field to physiological structures of the lung, a more readily recognisable image can be generated. This can be achieved by the further steps of:
3(a) segmenting a 3D image of the sample, and
3(b) associating segments of the 3D image with corresponding derivatives.

Figure 6:
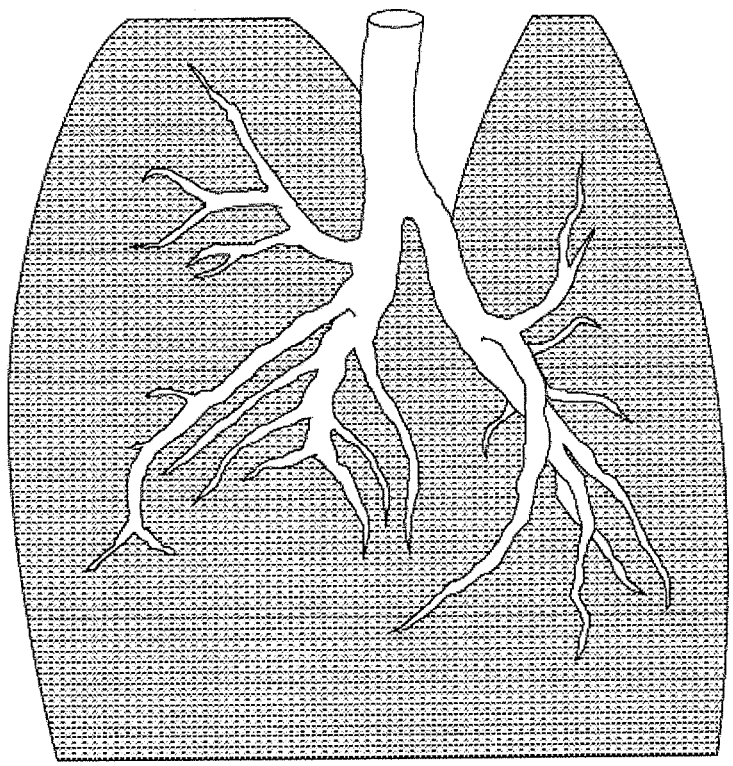
FIG. 6 is a 3D illustration of lung airway structure image according to the present invention, wherein the vectors of a velocity field have been matched to corresponding physiological features, being airways (trachea, bronchioles, alveoli)

FIG. 6 is an example of these further steps having been applied to create a 3D rendering of the lung airway structure. The motion of the lung tissue as measured using CTXV has been used to calculate the expansion of the lung, and hence the flow of air into the lung on a regional basis. The major airways are depicted in shades of grey (or preferably, different colours) to demonstrate different volume flows in different regions.

Accordingly, lung tissue motion data (FIG. 5) is processed using step 3 outlined above to establish measurement of air motion within the lung (FIG. 6). This 'two part' approach has an advantage over direct measurement of fluid motion in so far as a much lower dose of radiation can be used.

A similar two part approach could be applied to measurement of motion in other organs such as the heart. Specifically, it would be possible using the methods of the present invention to directly measure the flow or blood. It would also be possible using the methods of the present invention to measure motion of heart tissue (muscle wall, valves and/or vessels) and then derive measurement of fluid (blood) flow.

System & Apparatus

The method of the present invention could be implemented in a wide range of imaging systems. Preferably the method would be implemented using a CTXV system because this has the advantage of offering the best resolution and penetration of all medical imaging modalities.

A typical CTXV system incorporating the present invention would consist primarily of a number of phase contrast X-ray imaging lines—typically at least three imaging lines. More than three lines would improve the quality of the data collected, but would concomitantly increase system complexity, cost and potentially the X-ray dosage delivered.

With reference to FIG. 1, each imaging line would typically consist of the following key components:
a. video speed or double shutter X-ray camera (1);
b. cone beam X-ray source (2);
c. source modulation system (3);
d. basic source alignment hardware (4);
e. high-resolution camera alignment hardware (4);
f. image capture and analysis hardware (5); and
g. user interface (6).

In addition to the imaging hardware, there is a requirement for image capture and analysis hardware and software. The image capture and analysis hardware and software would typically consist of the following key components:
h. high speed image capture hardware;
i high speed image processing hardware;
j. image processing software; and
k. user interface for alignment, imaging and analysis.

Details of suitable components or component groups are described in the following paragraphs:

Cone Beam X-Ray Source:

As is typical of phase contrast sources there exists a trade off when considering the size of the source. Larger sources afford less contrast, but more light and hence shorter exposure times. Many current phase contrast systems employ so called micro or nano sources that are smaller than 5 micron. Typically, commercial 'off-the-shelf' sources of at least 20-50 micron in size would be suitable for use in the method and system of the present invention.

Source Modulation System (X-Ray Shutter):

Freeze frame photography is required for motion measurement. The continuous light sources must be modulated into short bursts with as close to a temporal square wave as possible. Complete control of exposures between 2 and 20 milliseconds are preferred. The use of a fast shutter also allows minimisation of the delivered dose, as the sample will be exposed to X-rays for the minimum time required for image capture.

Basic Source Alignment Hardware:

Optimally, the X-ray source is positioned so that the brightest region of the source is centred on the sample region of interest.

Video Speed or Double Shutter X-Ray Camera:

System measurement can be based on two or more raw images from each imaging line. These images must be taken in quick succession (at video frame rate or better). A camera system capable of sustained video frame rates or a 'double-shutter' camera with the capacity to acquire two images in quick succession will be required. If the optimal pixel size, minimum frame rate, and sensitivity are determined, a suitable commercial 'off-the-shelf' camera having the correct specification could be used.

High-Resolution Camera Alignment Hardware:

The system preferably includes automated, robotic alignment of each camera with respect to its respective source and any other cameras.

High Speed Image Capture Hardware:

A commercial 'off-the-shelf' data acquisition system can be used to control the cameras and capture the date from each imaging line at a speed that will allow analysis to progress almost in real time.

High Speed Image Processing Hardware:

Suitable options include, for example, GPU, FPGA or DSP processing platforms.

Image Processing Software:

A description of suitable software can be found for example, in Dubsky S, Jamison R A, Irvine S C, Siu K K W, Hourigan K and Fouras A (2010) *Computed tomographic X-ray velocimetry*, Applied Physics Letters 96(2), 023702. The software needs to be able to carry out a reconstruction according to the method of the present invention. Using the embodiment of the invention depicted in FIG. 3 as an example, the software may be able to discretise sample images into rectangular interrogation windows and perform cross-correlation on these windows. The volume may then be reconstructed in axial cross-sections, defined by the rows of the interrogation windows. A rectangular grid model may then be used to define the cross-sectional velocity profile. Cross-correlation functions can then be estimated from each interrogation window measurement region. The 3D velocity field reconstruction then becomes a minimisation of the error between the cross-correlation functions estimated using the velocity model, and those calculated from the X-ray image pairs, for all projection angles. The solution can be implemented using the Levenberg-Marquardt algorithm which performs a nonlinear least-squares optimisation.

User Interface for Alignment, Imaging and Analysis:

The central control system and user interface preferably allows simple activation of technical functions such as testing, calibration and alignment. The interface preferably also allows control of other user related functions such as imaging, image processing and visualisation of reconstructed results.

EXAMPLES

The present invention has been successfully used in 4 distinct animal trials on the Spring-8 synchrotron. These trials have studied;
  a. ventilator induced lung injury,
  b. bleomycin induced fibrosis,
  c. asthma based on the methacholine challenge and salbutamol reversal, and
  d. cystic fibrosis lung disease.

All four of these trials clearly demonstrated the use of the invention for measuring lung motion to provide early, accurate and regional detection of abnormal lung function. In some cases the detection of pathology was possible with lung motion measurement before it would be clear from histology or biopsy. This approach would also be useful for diagnosis of other diseases such as lung cancers.

The present invention will now be further described with reference to the following non-limiting examples.

Example 1

In this example the method of the present invention has been applied to the measurement of a strongly 3D flow.

The relevant imaging setup is shown in FIG. 1. The monochromatic beam in this case passes through a particle-seeded fluid (hollow glass spheres in glycerine). X-rays are slightly refracted at the interfaces between materials. The transmitted and refracted rays are allowed to propagate and interfere before being co-converted into visible light by the scintillator. This is then imaged using a high-speed detector and visible light optics, resulting in a phase contrast projection image. The image results from the superposition of interference fringes generated by the particle-liquid interfaces creating a dynamic speckle pattern that faithfully follows the particles.

Unlike visible light based imaging systems, in which images contain focus or holographic information from which depth can be inferred, the transmission nature of CTXV results in 2D volumetric projection image in which the entire volume is in focus, and therefore contains no information of the distribution of velocity in planes parallel to the X-ray beam propagation direction. Furthermore, from any single viewing angle only two components of displacement can be determined. This information deficit is overcome by rotating the sample and imaging from multiple projection angles, allowing tomographic reconstruction of the velocity field within the volume. From these multiple projections, simultaneous tomographic reconstruction of the object structure is also possible.

Forward Projection

Figure 3A:
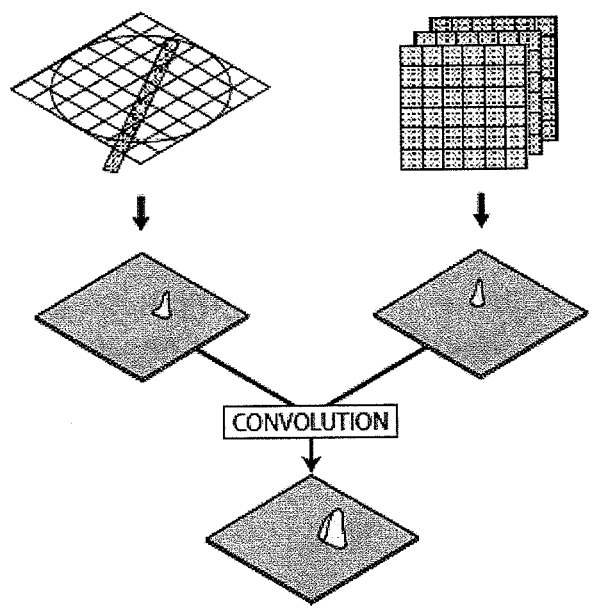
FIG. 3A is a schematic of the forward projection model according to the present invention. Cross-correlation functions are estimated by convolution of the velocity PDF, projected from the flow model, with the auto-correlation function calculated from the projection images.

As in traditional PIV, particle image pairs are discretised into interrogation regions and cross-correlation is performed on these regions FIG. 3A However, due to the large velocity distribution within the projected interrogation region, the cross-correlation functions will be highly distorted. The resulting projected cross-correlation statistics can be modelled as the velocity probability density function (PDF) of the flow projected onto that sub-region of the image (FIG. 3B), convolved with the particle image auto-correlation function FIG. 3D. Therefore if the flow field and particle image auto-correlation function are known, the cross-correlation functions that would theoretically result from the flow field can be estimated. This represents the forward projection model (see FIG. 3D. CTXV provides a solution of the inverse problem of reconstruction the flow field from the known cross-correlation data.

The effect of finite exposure time on the cross-correlation function of projection image pairs, must also be taken into account. Due to motion of the particle during the exposure, the contribution of each velocity to the cross correlation function will be stretched along the direction of that velocity, with a magnitude that is linearly proportional to that velocity. As this effect has been well characterised it can be easily accommodated into the forward projection model to eliminate any errors due to this phenomenon.

Solution to the Inverse Problem

FIGS. 3B to 3E demonstrates the implementation of CTXV. The velocity field is reconstructed in slices orthogonal to the axis of rotation FIG. 3B, concurrent with the rows of interrogation regions within the projection images FIG. 3D. A rectangular grid model represents the flow-field in the reconstruction domain. The three velocity components are defined at each node point in the model and bi-linear interpolation is used to define the flow between node points. Higher degree interpolation schemes may be used, such as spline interpolation at the expense of computation time and robustness.

Cross-correlation functions are estimated using the method shown in FIG. 3A. The convolution is effected through a Fast Fourier Transform (FFT) implementation. A Levenberg-Marquardt algorithm is utilised to minimise the error between the cross-correlation functions estimated from the flow model and those measured from the projection image pairs, resulting in a calculated flow model which accurately represents the flow-field. As the problem is heavily over-specified, a Tikhonov-type regularisation scheme is used to ensure convergence of the reconstruction, where the regularisation function is equal to the sum of the difference between each node velocity value and the mean value of its neighbours.

One-Dimensionalisation of the Cross-Correlation

In order to reduce the number of optimisation parameters and memory required for the reconstruction, a one-dimensionalisation of the cross-correlation functions is performed, allowing separate reconstruction of the date for $v_r$ and $v_q$. Projection of the cross-correlation data results in two one-dimensional representations of the function, for each of the velocity components $v_r$ and $v_q$, as illustrated in FIG. 3E. By separating the two components they can be reconstructed individually, greatly reducing the number of optimisation parameters required per reconstruction. Furthermore, the process significantly reduces the amount of data that needs to be stored and analysed.

Simultaneous Structure Reconstruction

To model the forward projection of the velocity PDF correctly, the relative particle seeding density with in the reconstruction domain must be known. Assuming homogenous seeding within the working fluid, this corresponds to knowledge of the flow geometry. According there is provided a CT technique that allows the flow geometry to be reconstructed using the date obtained during the CTXV scan.

In typical CT reconstruction techniques, integrated object density in the projection direction is calculated from the X-ray transmission, which will be proportional to pixel intensity values on a digital projection image. In the case of a material of constant density, this integrated object density will be proportional to the object thickness. The contrast of the particle speckle (defined as the ratio of the standard deviation of the image intensity to the mean intensity) will increase with the square root of object thickness and so this statistic may also be sued for tomographic reconstruction of the object's structure. This is advantageous, as in many cases, including in vivo imaging of blood vessels the absorptions contrast alone is insufficient for tomographic reconstruction. Furthermore, the motion of the particle between images taken at different projection angles results in artifacts in the subsequent reconstructions. In comparison, the particle speckle contras will be stationary for all viewing angles. The particle speckle contrast is calculated for discrete sub-regions in each phase contras image, prior to phase retrieval. The flow geometry is reconstructed from the particle speckle contrast data using an algebraic reconstruction technique. The use of an algebraic technique allows for accurate reconstructions with low numbers of projections.

Example 2

Figure 2:
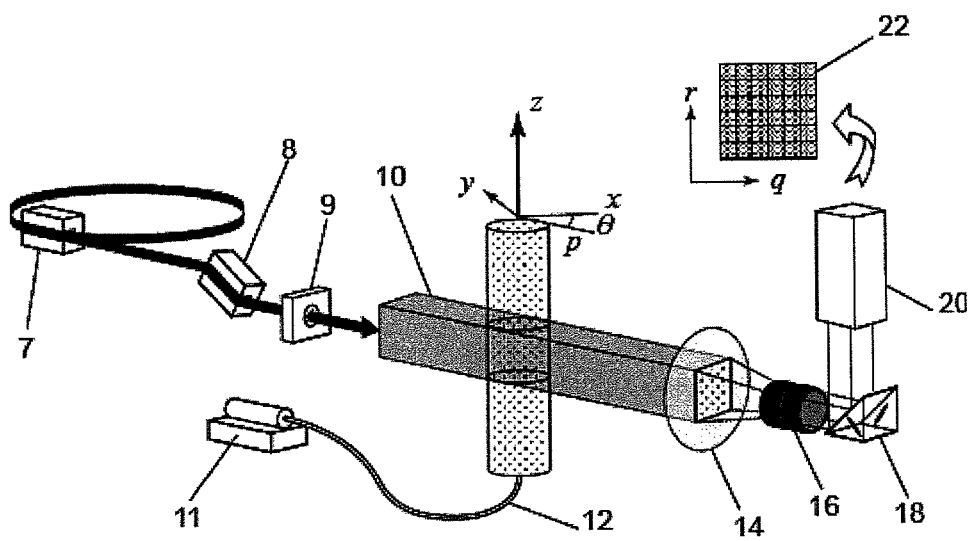
FIG. 2 is as schematic diagram of experimental imaging setup illustrating Cartesian coordinates x, y, z fixed to the sample, and rotated at an angle θ– from the beam axis p. The diagram shows a monochromatic X-ray beam transmitted through a sample and converted to visible light by a scintillator. A high-speed detector system then produces an image. Multiple projection data are gathered by rotating the sample. Cartesian co-ordinates (x,y,z) are fixed to the sample and rotated at an angle θ from the beam axis p.

In this example experiments are described which demonstrate the application of CTXV to the simultaneous measurement of structure and velocity. The method of the present invention was used with a high resolution medical imaging beam-line (BL20XU) on a Spring-8 synchrotron at Hyogo, Japan set up as shown in FIG. 2. The source to sample distance of 245 meters provides highly coherent X-rays for phase contrast imaging. A Si-111 double crystal monochromator was used to provide a monochromatic beam energy of 25 KeV.

Sample

The sample comprised an optically opaque plastic arterial model, with an average diameter of 950 μm, manufactured using a 3D-printing technology. The model was manufactured out of the Objet™ FullCure® acrylic-based photopolymer material. The high resolution technique, with a layer thickness of 16 μm, ensured the models were accurate on the small scale being investigated. The geometry was chosen to mimic a stenosed artery, generating a three-dimensional flow field similar to that which would occur in vivo. Blood was pumped through the model at a flow-rate of 4.8 μl/mn, using a syringe pump (WPI Inc. UMP2). While PCI has been successful in imaging red blood cells as PIV tracer particles, to increase signal to noise ratio the blood was seeded with gas micro-bubbles. As PCI creates high contrast at a gas-liquid interface, microbubbles represent an ideal flow tracing media for this imaging modality. The ultrasound contrast agent Definityr (Bristol-Myers Squibb Medical Imaging Inc) was used. When activated, Definityr forms a stable, injectable, homogeneous suspension of perfluorocarbon-filled microbubbles, with a mean diameter of 2.5 μm.

Data Collection

The imaging setup is shown in FIG. 2. From a synchrotron storage ring (7), an X-ray beam is passed through a monochromator (8) and its emission is controlled by an X-ray shutter (9). The X-ray beam (10) projects in direction p through the sample (12) which flows in the direction z under control of a syringe pump (11). The X-ray beam (10) then impinges on a scintillator (14), which converts X-ray radiation into visible light. The scintillator is imaged using a high-speed intensified CMOS detector (20) (IDT Inc. X5i, 4 megapixel) through a microscope objective lens (16), resulting in a magnification of approximately 15×, or an effective pixel size of 0.52 μm. An optical mirror (18) removes the detector from the X-ray beam (10) path. A total scan time of less than 10 seconds was achieved through the use of a high-speed intensified camera, which allowed exposure times of 4.5 ms, and a frame rate of 200 Hz. The sample was rotated through 9 projection angles, spaced over 180 degrees, with 195 images taken at each angle to provide a particle projection image (22). The sample to detector distance was optimized experimentally for phase contrast of the blood-Definity® mixture, and an optimum of 900 mm was found to provide the best signal.

Image Pre-Processing

X-ray phase contrast particle images require pre-processing prior to cross-correlation analysis. A spatial high-pass filter was applied to remove the effects of inhomogeneous illumination. Stationary structures such as the vessel walls, monochromators effects, and dust on the detector or associated optics, are removed by average image subtraction. A single-image phase-retrieval algorithm as described by Paganin et al (Paganin D, Mayo S C, Gureyev T E, Miller P R and Wilkins S W 2002 *Journal of Microscopy* 206(1):33-40) is then implemented to remove phase contrast fringes and improve the images for cross-correlation analysis, as described by Irvine et al (Irvine S C, Paganin D M, Dubsky S, Lewis R A and Fouras A 2008 *Applied Physics Letters* 93:153901).

Velocity Reconstruction

Figures 3B, 3C, 3D:
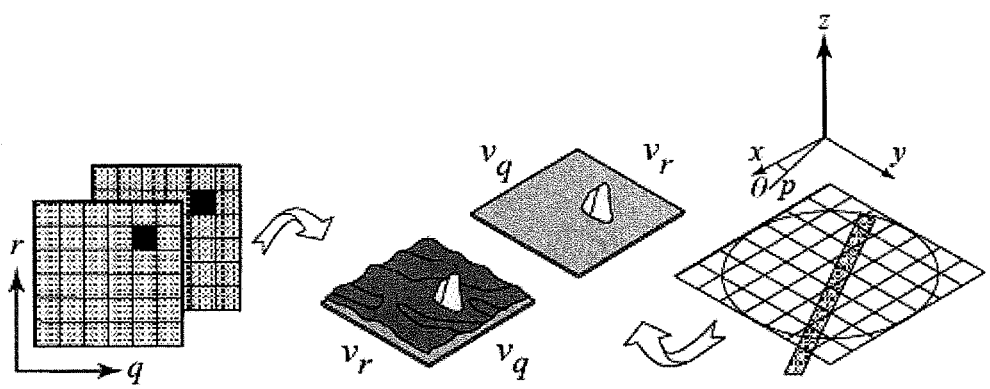
FIG. 3B illustrates 3D CTXV motion reconstruction, the residual between estimated and measured cross-correlations having been minimized over all interrogation windows and all projection angles simultaneously to yield a cross-sectional flow model which accurately represents the flow field.
FIG. 3C illustrates one-dimensionalisation of the cross-correlation functions. Integration across the rows and columns in the 2D cross-correlation function yields a 1D representation of the velocity PDF in the r and q directions respectively.
FIG. 3D illustrates the forward projection model based on data contributed from FIGS. 3A to 3C.
Figure 3E:
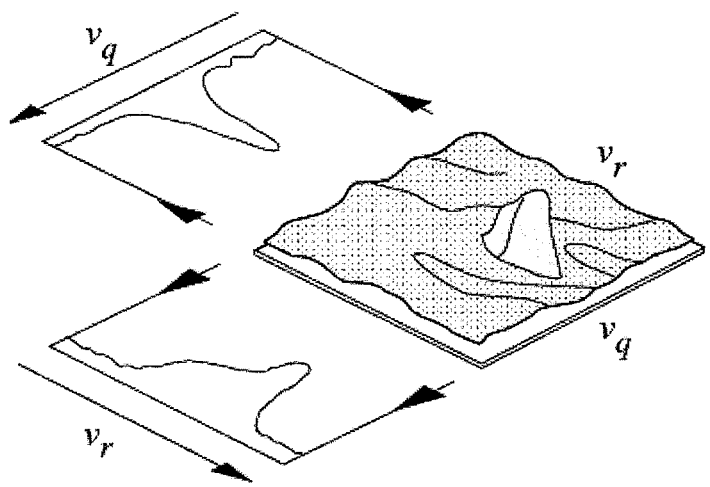
FIG. 3E illustrates the projection of the cross-correlation data results in two one-dimensional representations of the function, for each of the velocity components $v_r$ and $v_q$.

FIG. 3 outlines the reconstruction method used. The particle images are allocated into rectangular interrogation windows and cross-correlation is performed on these windows between projection image pairs (FIG. 3A). The volume is reconstructed in axial cross-sections, defined by the rows of the interrogation windows. A rectangular grid model is used to define the cross-sectional flow profile (FIG. 3C). Velocity components in the x, y and z directions, $v_x$, $v_y$, and $v_z$, are defined at each node in the model. Bi-linear interpolation is used between node points to define the velocity profile in the model space. A point on the model P(x,y) will be projected onto the image plane as P(q), where, $q=y\cos(\theta)-x\sin(\theta)$ for a given cross-section in z. Similarly, velocity components are transformed onto the image plane as $$v_q = v_y \sin(\theta) - v_x \cos(\theta)$$

$$v_r = v_z$$

where vq and vr are the velocity components in the q and r directions.

Cross-correlation functions are estimated for each interrogation window measurement region by projecting the PDF from the flow model onto the image plane. This projected PDF is convolved with the image auto-correlation function to yield the estimated cross-correlation functions. The 3D velocity field reconstruction then becomes a minimization of the error between the cross-correlation functions estimated using the flow model, and those calculated from the X-ray image pairs, for all projection angles (FIG. 3C). The solution is implemented using a non-linear least-squares solver.

Figure 4:
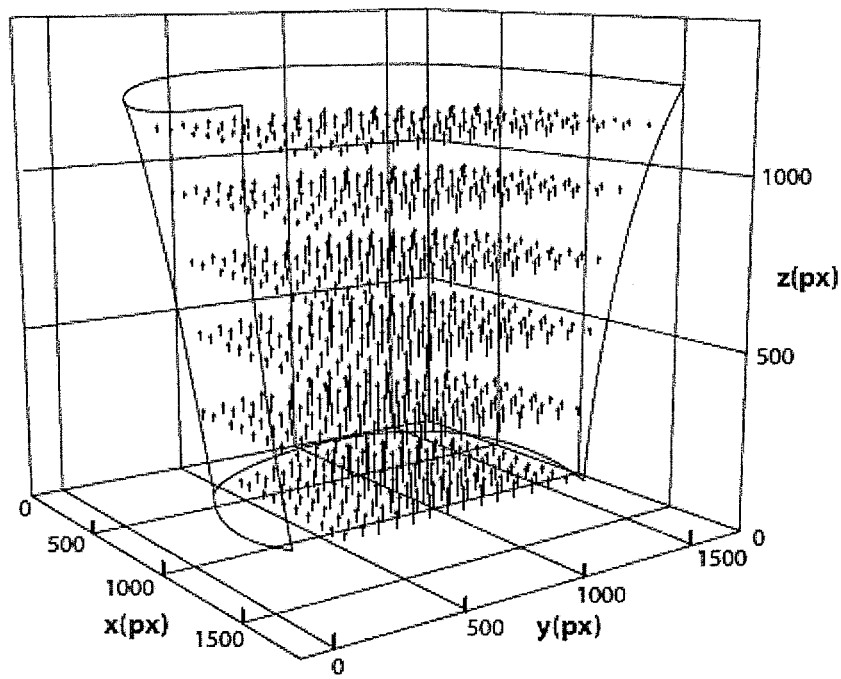
FIG. 4 illustrates a 3D reconstructed blood velocity field at a single time point. For clarity only half the sample is plotted, with reduced vector resolution in all dimensions so that individual vectors can be seen. The vectors are depicted in different colours, with each colour representing a different velocity magnitude.

FIG. 4 shows the 3D velocity field of blood flow inside the optically opaque vessel model. Maximum velocity reduces as the vessel geometry expands, as predicted by the conservation of mass. Independently reconstructed cross-sections are self-consistent with respect to volume flow rate to within 2%, and are consistent with the syringe pump setting. The result demonstrates the ability of the present invention to measure all three components of velocity within a volume, with no optical access required.

Example 3

In this example a further experiment is described which demonstrate the application of CTXV to the simultaneous measurement of structure and velocity. The method of the present invention is again used with a high resolution medical imaging beam-line (BL20XU) of the Spring-8 synchrotron at Hyogo, Japan.

Sample

The sample used was an opaque plastic model with a complex three-dimensional geometry (FIG. 7A), manufactured using Object rapid prototyping technology. The test section consisted of a solid cylinder of 14 mm diameter, with a hollow section allowing internal flow of the working fluid. The geometry of the hollow section was constructed as the union of a cone and a helically swept circle, resulting in corkscrew geometry with a decreasing cross-sectional area. The geometry was chosen to exhibit a strongly three-dimensional flow. The working fluid, glycerine seeded with 35 um (nominal) solid glass spheres was pumped through the model at 0.1 ml/min using a syringe pump. The propagation distance, defined as the distance form the front face of the object to the scintillator was optimised for maximum signal to noise ratio of the glycerine/glass mixture at 6 m.

Data Collection

The imaging setup was that shown in FIG. 2 and describe with reference to Example 2. Specifically the BL20B2 beam-line used a bending magnet insertion device. An X-ray energy of 25 keV was selected using an Si-111 monochromator. A fast X-ray shutter was used to minimise sample dose and also to protect the P43 scintillator from the high flux X-ray beam. An EM-CCD detector (Hamamatsu C9100-02) was sued for its sensitivity and low noise characteristics. The optics used resulted in an effective pixel size of 9.5×9.5 µm², allowing a field of view of 9.5 mm×9.5 mm. Images were acquired at 19 angles, evenly spaced over 180° (inclusive). The 180° projection was included to allow the calculation of the centre of rotation of the sample; however this may be excluded in place of simple calibration/alignment process. The detector acquired images at 28.5 frames per second with an exposure time of 30 ms.

Velocity Reconstruction

Figures 7A, 7B:
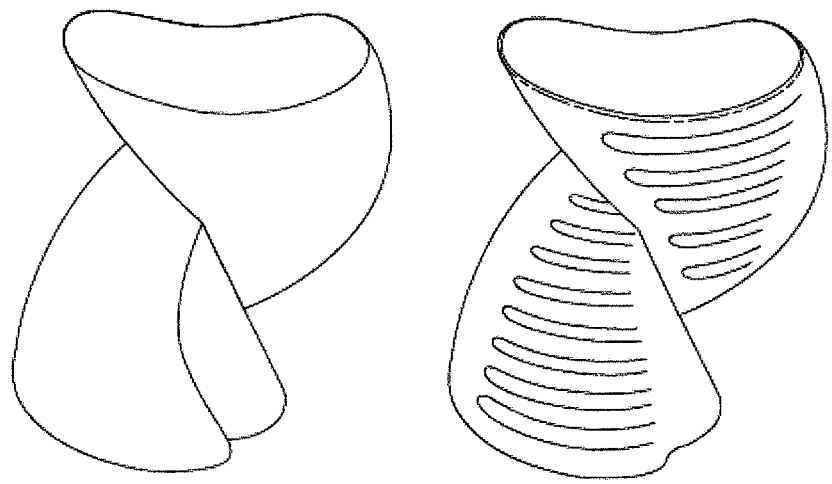
FIG. 7A illustrates a computer aided design model for the hollow section of the sample of Example 3.
FIG. 7B illustrates a CT reconstruction based on particle speckle contrast of the hollow section of the sample of Example 3. The sample geometry is based on the union of a cone and a helically swept circle.

The flow geometry was reconstructed using the method described in Example 1. A substantially higher signal was achieved using the particle speckle contrast data (as compared with using the raw phase contrast image. The speckle contrast map was generated using 16×16 px² sub-regions with 50% overlap. FIG. 7 shows the computer aided design (CAD) model (FIG. 7A) used for the manufacture of the hollow section of the flow model and the tomographically reconstructed geometry, segmented using at gradient-based edge detection method (FIG. 7B).

Figure 8:
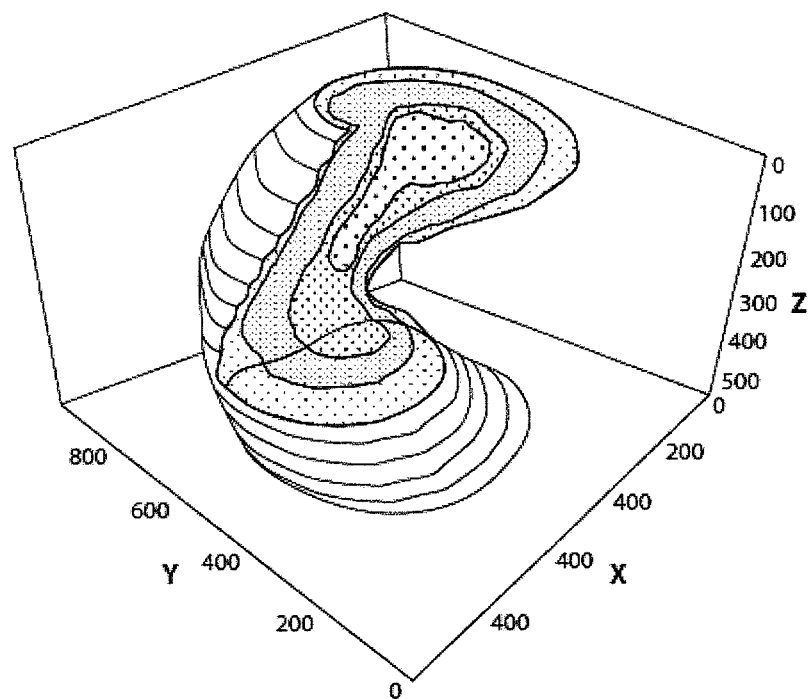
FIG. 8 illustrates a CTXV reconstruction of flow through the sample depicted in FIG. 7 to show how CTXV can simultaneously measure the 3D structure and velocity of flow through complex geometries. A section of the image has been rendered transparent to enable the flow and vectors within the sample to be seen, and for clarity, vector resolution is reduced by 4× in the x, y and z directions.

For the velocity reconstruction, cross-correlation function ere calculated using 64×64 px² interrogation windows with 75% overlap. Correlation averaging was used with an ensemble of 99 image pairs taken at each projection angle to produce the averaged correlation data. The 69 axial slices were individually reconstructed on a rectangular grid of approximately 300 node points, depending on the size of the object within each slice, interpolated onto a 124×124 px² sub-grid. The resulting structure and velocity fields are shown in FIG. 8. As expected, the flow follows the helical geometry, increasing in speed as the vessel constricts through the cone section. The results illustrate the ability of the technique to measure complex 4D flows, even with few projections.

Example 4

This example describes the coupling of PIV with phase contrast X-ray imaging (PCXI) for detection of lung tissue movement and for measurement of the velocity fields that define speed and direction of regional lung motion through a breath. Regional maps of the lung are generated to show the degree and timing of expansion from the velocity fields, revealing regions of abnormal tissue properties cause by experimentally induced non-uniform lung disease.

Methods

Animal Studies:

Adolescent Balb/c nude male mice were exposed to bleomycin (20 mg/kg body weight in 20 ul saline. Sigma, n=8) or saline (20 ul; n=6) by intranasal instillation under isoflurane anaesthesia. During imaging mice were anesthetized (Somnopentyl; 15 mg/kg i.p.) and muscle relaxed (Mioblock 1 gh/kg i.m.), then surgically intubated and placed in a pre-warmed (37° C.) water column for ventilation and imaging. Mice were then humanely killed (Somnopentyl; 100 mg/kg i.p.); the lungs were excised and pressure fixed at 20 cm $H_2O$ in 10% formalin. Paraffin embedded lung sections (5 um) stained with Massons Trichrome were used to determine the Ashcroft score; five fields of view from at least three randomly selected lung sections/mouse. Unpaired one-tailed T-tests were used to compare mean tidal volume and parameters for the Ashcroft score. Two-way repeated measures ANOVA was used to determine differences in frequency distributions of lung expansion and time f lung expansion. Results were considered statistically significant at a probability level of 5%. Values are reported as mean+/− SEM (unless stated otherwise).

Mice were examined during two separate experiments with a total for four groups (n=14). Each experiment consisted of two groups: controls (n=3) and a group treated with bleomycin (n=4), with measurements performed at 36 hours and 6 days after exposure. Mouse exposure to bleomycin causes progressive lung injury. Inhaled bleomycin is a well characterised and commonly used experimental model of pulmonary fibrosis that begins with the initiation of an inflammatory cascade. Since Balb/c nude mice (an immune-deficient strain) were utilised in the study, it is not surprising that the pulmonary fibrotic response was reduced in these mice compared with reports in other strains because inflammatory responses are reduced in these mice.

X-Ray Imaging:

X-ray imaging was conducted using the high resolution medical imaging beam-line (BL20XU) on a Spring-8 synchrotron at Hyogo, Japan set up as shown in FIG. 2. Propagation based phase contrast imaging was conducted at 25 keV with a sample-to-detector distance of 2 m. X-ray photons were converted to visible light using a Hamamatsu Beam Monitor (BM5) and acquired by a Hamamatsu EMCCD (C9100-02) camera. Images were acquired with an exposure time of 20 ms, an interframe time of 34.5 ms and an effective pixel size of 19 um. Image acquisition was synchronised with ventilation with 70 frames acquired during inspiration and 30 frames during expiration.

Velocimetry Analysis:

Velocimetry analysis use custom software. Bulk animal motion was calculated and removed from image sequences by PIV analysis of upper vertebrae, followed by interpolation of images onto a static reference frame. Lungs were isolated from images by band-pass filtering based on appropriate frequency cut-offs. Regions of image occupied by lungs were identified and masked with velocimetric analysis of lung tissue motion conducted over masked regions for 5 consecutive inspirations. These data were then phase-averaged, resulting in a data set of 70 frames of velocimetry representing the inspiration phase of respiration for each animal. At every time-point, the local rate of expansion can be expressed as the divergence of the vector field where the spatial derivates are accurately and easily evaluated from the velocity vector field. The total expansion over inspiration is the sum of the expansion between each pair of subsequent time points. As the data was integrated over the entire inspiration, total expansion was represented in a single map. If the vector field could be measured in 3 dimensions (3D) over time, then the 3D quantification of expansion would be directly related to regional compliance, and the average time of compliance directly related to airway resistance. To preserve the temporal quality of the expansion map, while still reducing the volume of data, a map of the time at which the average expansion occurred was developed. The average time was evaluated as the sum of the product of expansion and time, normalised by the sum of the expansion.

Velocimetry Application

Projection of the X-ray beam through multiple overlying airways produced high contrast speckle intensity patterns whose movement over subsequent X-ray images takes the place of the introduced tracker particles used in conventional PIV. By adapting the analysis methods of PIV to phase contrast X-ray images; a comprehensive map of regional lung velocity over the breathing cycle was generated.

Figure 9A:
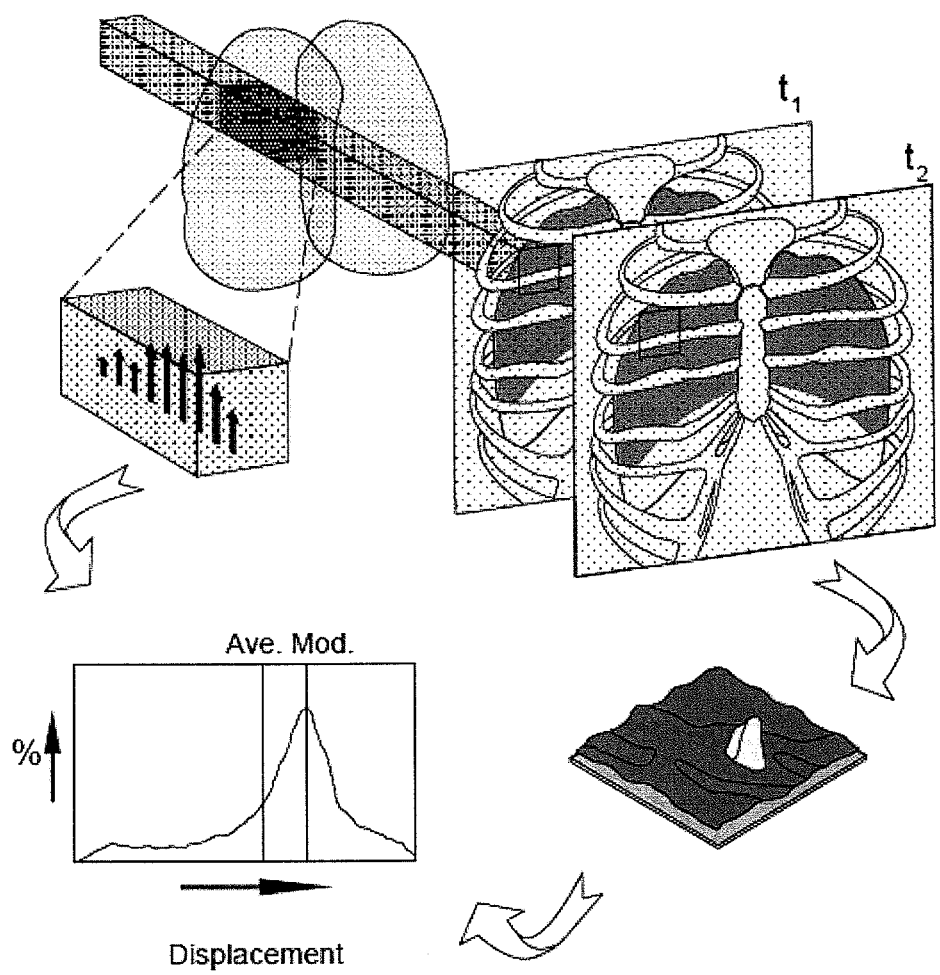
FIG. 9A shows the 3D nature of X-ray illumination and velocimetric cross-correlation analysis as described in Example 4.
Figure 9B:
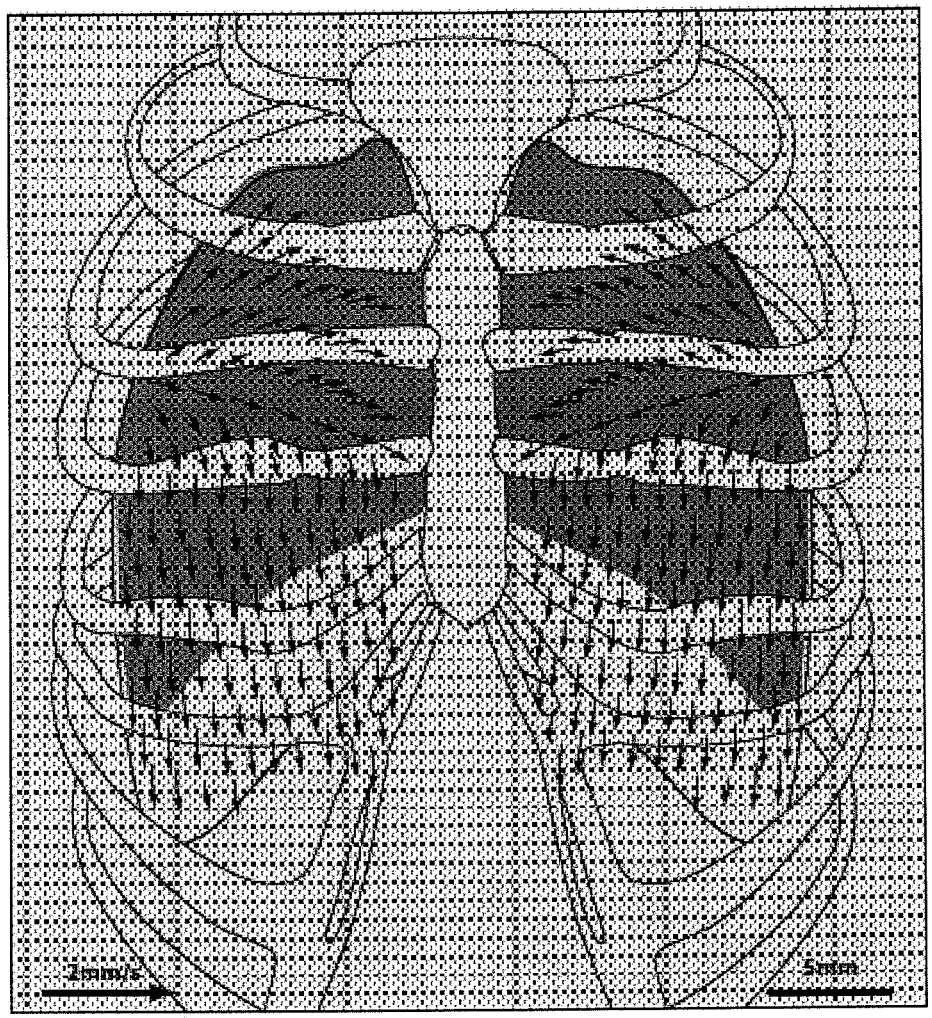
FIG. 9B illustrates in vivo detection of lung tissue motion according to the present invention.
Figure 10A:
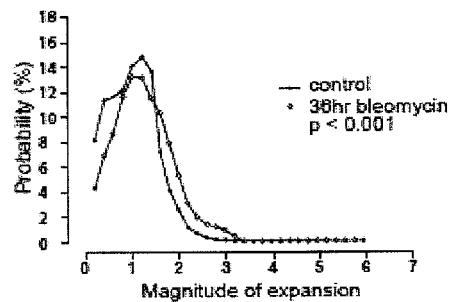
FIG. 10A depicts statistical measures of lung pathology in terms of the magnitude of lung expansion comparing control groups with test groups 36 hours after bleomycin exposure.
Figure 10E:
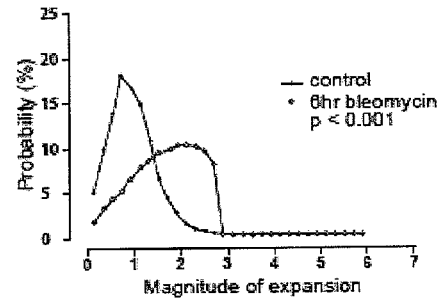
FIG. 10E depicts statistical measures of lung pathology in terms of the magnitude of lung expansion comparing control groups with test groups 6 hours after bleomycin exposure.
Figure 10B:
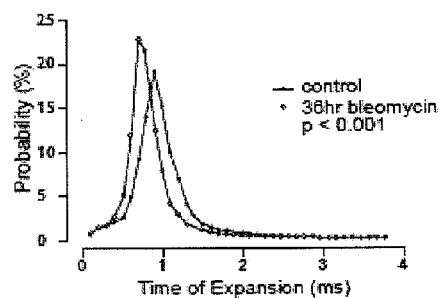
FIG. 10B depicts statistical measures of lung pathology in terms of the time taken for lung expansion (ms) comparing control groups with test groups 36 hours after bleomycin exposure.
Figure 10F:
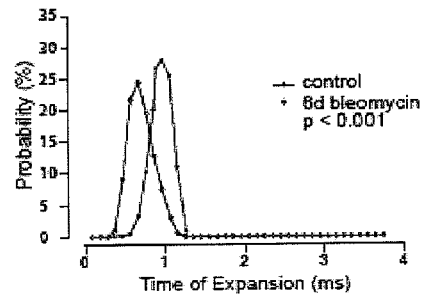
FIG. 10F depicts statistical measures of lung pathology in terms of the time taken for lung expansion (ms) comparing control groups with test groups 6 hours after bleomycin exposure.
Figure 10C:
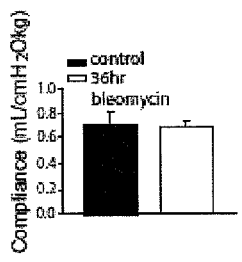
FIG. 10C depicts rates of compliance (mL/cmH$_2$Okg) of the control groups and test groups of FIG. 10A and FIG. 10B.
Figure 10D:
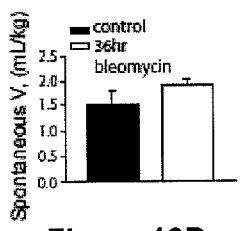
FIG. 10D depicts spontaneous volume (mL/kg) in the control groups and test groups of FIG. 10A and FIG. 10B.
Figure 10G:
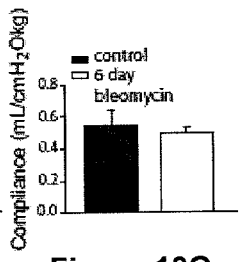
FIG. 10G depicts rates of compliance (mL/cmH$_2$Okg) of the control groups and test groups of FIG. 10E and FIG. 10F.
Figure 10H:
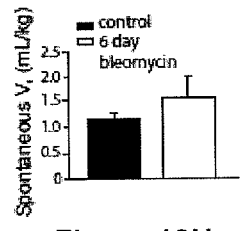
FIG. 10H depicts spontaneous volume (mL/kg) in the control groups and test groups of FIG. 10E and FIG. 10F.
Figure 12:
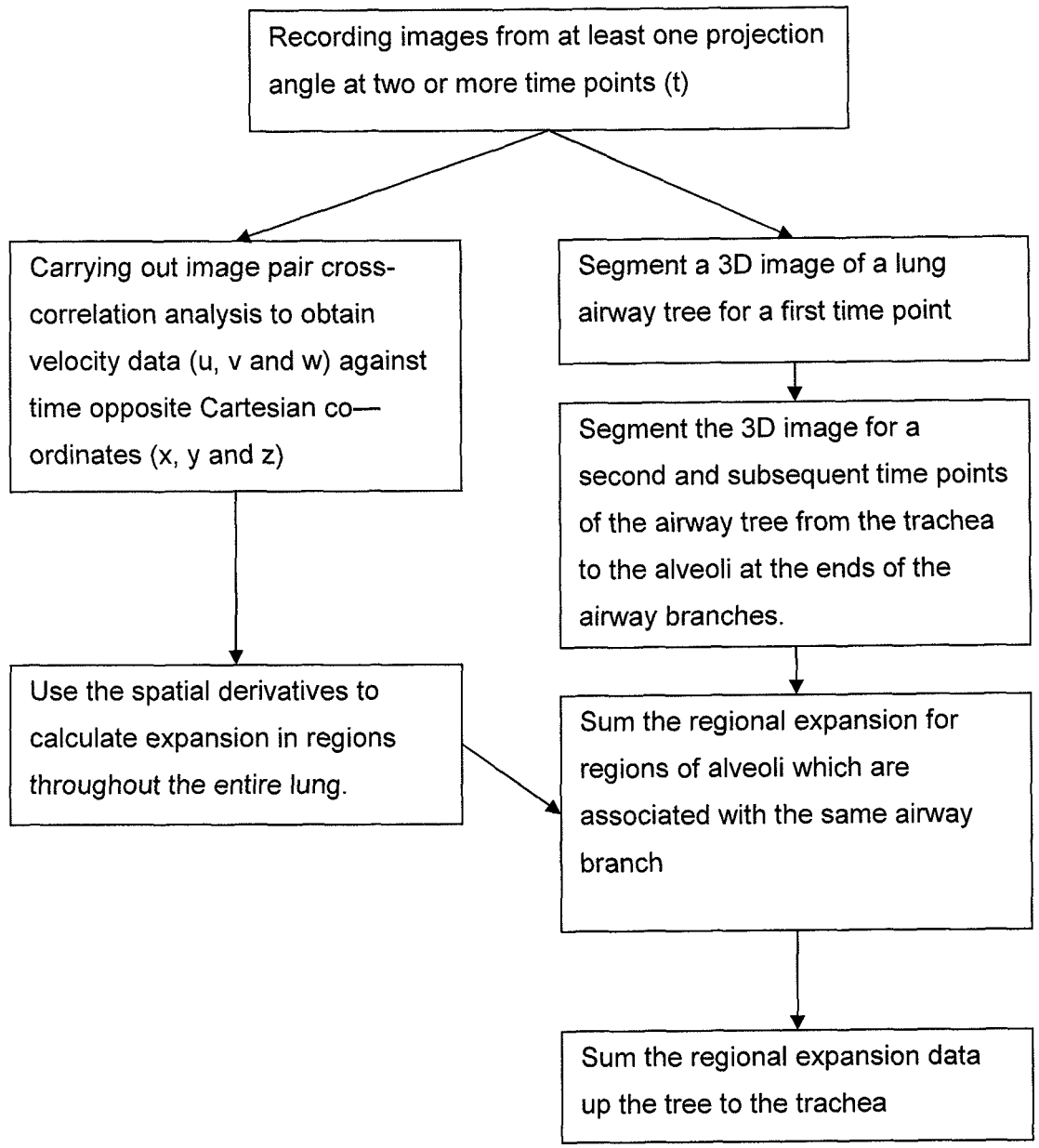
FIG. 12 is a flow chart depicting a preferred embodiment of the steps of the method of the present invention.

FIG. 9A shows the 3D nature of X-ray illumination and velocimetric cross-correlation analysis. Each 2D sampling region in the projection images represents a 3D volume for which a distribution of velocities may be present. The present analysis selects the modal velocity which may differ significantly from the mean. FIG. 9B depicts this in vivo detection of lung tissue motion. Specifically, in this example, lung images were divided into 2641 overlapping segments with a velocity vector associated with each segment. The spacing between each velocity measurement was 155 um, which is of similar dimensions to a single alveolus. One hundred images were acquired per breath over 5 breaths and the complete data set was used to generate movies that demonstrate the temporal pattern of the change in speed and direction of lung motion throughout a breath. The velocity was measured relative to the upper vertebrae, the motion of which was measured and then removed form the image sequences prior to analysis.

Lung tissue motion is a complex function of the local characteristics of regional compliance, the compliance and motion of nearby tissue, as well as the proximity to structures such as the diaphragm, heart and chest wall. For example, lung tissue near the diaphragm displayed significantly more motion than tissue near the apex of the lung, irrespective of the local compliance. To accommodate differential degrees of motion across the lung, two measures of compliance were developed and evaluated: the local rate of expansion and the average time of expansion—both normalised using the average for all controls within their experiment.

FIG. 10 depicts statistical measures for lung pathology comprising controls with groups 36 hours after bleomycin exposure (FIGS. 10A to 10D) and 6 days after exposure (FIGS. 10E to 10H). Frequency distribution of the magnitude of expansion (top, measured via velocimetry) is compared for treated groups (n=4) with controls (n=3). Datum were normalised by average of controls. At 36 hours post treatment, treated mice have 24% greater expansion on average and 14% of treated lungs expand at over 2× the control average compared with less than 5% for control lungs. At 6 days post treatment treated mice have 76% greater expansion on average and 47% of treated lungs expand at over 2× the control average compared with less than 4% for control lungs. Asterisks indicate significant difference between control and treated animals ($p<0.001$). Frequency distribution of the average time of expansion (middle) in control and treated mice are shown. Asterisks indicate significant difference between control and treated animals ($p<0.001$). Bottom:

comparisons of the compliance between control and treated mice (statistically insignificant) and Tidal volumes (VT)(tidal volumes in controls are significantly lower than treated groups) but are non specific and global in nature.

FIG. 11 shows regional expansion within the lung and comparative histological imagery. Maps of regional expansion (normally in colour) have been determined using PIV for typical control mice (FIG. 11A) and bleomycin-treated mice 6 days after exposure (FIG. 11B). Data are normalised by the average regional expansion across the control group and maps generated using a colour scale. The mice treated with bleomycin (FIG. 11B) had dramatic regional alterations in the pattern of lung expansion. Histological image FIG. 11C from the lung imaged in FIG. 11A is typical of the control group. Histological images FIGS. 11D and 11E from the lung imaged in FIG. 11B are typical of the diseased group 6 days after bleomycin treatment. Scale bars in FIGS. 11A and 11B show relative size of images and inset boxes for FIGS. 11C, 11D and 11E are shown to scale in FIGS. 11A and 11B.

While this invention has been described in connection with specific embodiments thereof, it will be understood that it is capable of further modification(s). This application is intended to cover any variations uses or adaptations of the invention following in general, the principles of the invention and including such departures from the present disclosure as come within known or customary practice within the art to which the invention pertains and as may be applied to the essential features hereinbefore set forth.

As the present invention may be embodied in several forms without departing from the spirit of the essential characteristics of the invention, it should be understood that the above described embodiments are not to limit the present invention unless otherwise specified, but rather should be construed broadly within the spirit and scope of the invention as defined in the appended claims. The described embodiments are to be considered in all respects as illustrative only and not restrictive.

Various modifications and equivalent arrangements are intended to be included within the spirit and scope of the invention and appended claims. Therefore, the specific embodiments are to be understood to be illustrative of the many ways in which the principles of the present invention may be practiced. In the following claims, means-plus-function clauses are intended to cover structures as performing the defined function and not only structural equivalents, but also equivalent structures.

It should be noted that where the terms "server", "secure server" or similar terms are used herein, a communication device is described that may be used in a communication system, unless the context otherwise requires, and should not be construed to limit the present invention to any particular communication device type. Thus, a communication device may include, without limitation, a bridge, router, bridge-router (router), switch, node, or other communication device, which may or may not be secure.

It should also be noted that where a flowchart is used herein to demonstrate various aspects of the invention, it should not be construed to limit the present invention to any particular logic flow or logic implementation. The described logic may be partitioned into different logic blocks (e.g., programs, modules, functions, or subroutines) without changing the overall results or otherwise departing from the true scope of the invention. Often, logic elements may be added, modified, omitted, performed in a different order, or implemented using different logic constructs (e.g., logic gates, looping primitives, conditional logic, and other logic constructs) without changing the overall results or otherwise departing from the true scope of the invention.

Various embodiments of the invention may be embodied in many different forms, including computer program logic for use with a processor (e.g., a microprocessor, microcontroller, digital signal processor, or general purpose computer), programmable logic for use with a programmable logic device (e.g., a Field Programmable Gate Array (FPGA) or other PLD), discrete components, integrated circuitry (e.g., an Application Specific Integrated Circuit (ASIC)), or any other means including any combination thereof. In an exemplary embodiment of the present invention, predominantly all of the communication between users and the server is implemented as a set of computer program instructions that is converted into a computer executable form, stored as such in a computer readable medium, and executed by a microprocessor under the control of an operating system.

Computer program logic implementing all or part of the functionality where described herein may be embodied in various forms, including a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM or DVD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and inter-networking technologies. The computer program may be distributed in any form as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality where described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM or DVD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web).

"Comprises/comprising" and "includes/including" when used in this specification is taken to specify the presence of stated features, integers, steps or components but does not preclude the presence or addition of one or more other features, integers, steps, components or groups thereof. Thus, unless the context clearly requires otherwise, throughout the description and the claims, the words 'comprise', 'comprising', 'includes', 'including' and the like are to be construed in an inclusive sense as opposed to an exclusive or exhaustive sense; that is to say, in the sense of "including, but not limited to".

The invention claimed is:

1. A method for presenting information derived from a sample, the method including the steps of:
   a. recording images from at least one projection angle and carrying out image analysis, encoding velocity data for the sample in terms of coordinates;
   b. reconstructing a 2D or 3D velocity field directly from the image analysis; and
   c. calculating the expansion of one or more regions in terms of velocity (u, v and w) against time opposite co-ordinates (x, y and z) and using derivatives defined by $\delta u/\delta x + \delta v/\delta y + \delta w/\delta z$ for textual or graphical presentation.

2. A method according to claim 1 wherein the reconstruction of step b is performed by first reconstructing 2D or 3D images.

3. A method according to claim 1 or 2 which further includes the step of:
   d. for one or more regions, using the expansion calculated in step c to calculate a parameter associated with motion.

4. A method according to claim 1 which further includes the step of:
   e. segmenting an image of the sample.

5. A method according to claim 4 which further includes the step of:
   f. associating each segment with regions of the 2D or 3D velocity field.

6. A system operative on the basis of presenting information derived from a sample, the system comprising an image capture means, a processor, and a user interface, wherein
   a. the image capture means records images from at least one projection angle and the processor carries out image analysis, encoding velocity data for the sample in terms of coordinates;
   b. the processor reconstructs a 2D or 3D velocity field directly from the image analysis; and
   c. the processor calculates the expansion of one or more regions in terms of velocity (u, v and w) against time opposite co-ordinates (x, y and z) and using derivatives defined by $\delta u/\delta x + \delta v/\delta y + \delta w/\delta z$ and is operative to present the calculated values as text or graphics.

7. A non-transitory computer readable storage medium for storing an application for executing a method of presenting information derived from a sample, the method including the steps of:
   a. recording images from at least one projection angle and carrying out image analysis, encoding velocity data for the sample in terms of coordinates;
   b. reconstructing a 2D or 3D velocity field directly from the image analysis; and
   c. calculating the expansion of one or more regions in terms of velocity (u, v and w) against time opposite co-ordinates (x, y and z) and using derivatives defined by $\delta u/\delta x + \delta v/\delta y + \delta w/\delta z$ for textual or graphical presentation.

* * * * *